(12) United States Patent
Mackenzie et al.

(10) Patent No.: US 11,313,799 B2
(45) Date of Patent: Apr. 26, 2022

(54) CALIBRATION OF A SENSOR

(71) Applicant: SciLogica Corp., Denver, CO (US)

(72) Inventors: Alasdair Allan Mackenzie, Herefordshire (GB); Barry Colin Crane, Oxon (GB); Nicholas Paul Barwell, Warwickshire (GB); Praveen Sagar, Bucks (GB); Robert Perkins, Oxfordshire (GB)

(73) Assignee: SciLogica Corp., Denver, CO (US)

( * ) Notice: Subject to any disclaimer, the term of this patent is extended or adjusted under 35 U.S.C. 154(b) by 11 days.

(21) Appl. No.: 16/792,563

(22) Filed: Feb. 17, 2020

(65) Prior Publication Data

US 2021/0255103 A1 Aug. 19, 2021

(51) Int. Cl.
*G01N 21/64* (2006.01)
*G01N 33/49* (2006.01)

(52) U.S. Cl.
CPC ..... *G01N 21/6402* (2013.01); *G01N 21/6486* (2013.01); *G01N 33/492* (2013.01); *G01N 2201/062* (2013.01); *G01N 2201/0612* (2013.01)

(58) Field of Classification Search
CPC ............. G01N 21/6402; G01N 33/492; G01N 21/6486; G01N 2201/0612; G01N 2201/062
See application file for complete search history.

(56) References Cited

U.S. PATENT DOCUMENTS

| 5,672,515 A | 9/1997 | Furlong | |
|---|---|---|---|
| 2008/0086044 A1* | 4/2008 | Brister | A61B 5/1495 600/365 |
| 2008/0215254 A1* | 9/2008 | Leiner | G01N 21/274 702/25 |

(Continued)

OTHER PUBLICATIONS

Tusa & He, J. Critical care analyzer with fluorescent optical chemosensors for blood analytes, Mater. Chem., 2005:15:2640-2647.

(Continued)

*Primary Examiner* — Marcus H Taningco
(74) *Attorney, Agent, or Firm* — Harness, Dickey & Pierce, P.L.C.

(57) ABSTRACT

There is provided a method of calibrating a sensor comprising a luminescent compound having a luminescence that depends on the concentration of an analyte, and a detector configured to detect light emitted by the luminescent compound, the method comprising providing a component comprising the luminescent compound in a package that maintains exposure of the luminescent compound to the analyte at a known first concentration, assembling the component into the sensor and measuring a first value of a characteristic of the luminescence of the luminescent compound while exposed to the analyte at the first concentration, measuring a second value of the characteristic of the luminescence of the luminescent compound while exposed to the analyte at a known second concentration different from the first concentration, and determining parameters representing the (Continued)

dependence of the characteristic of the luminescence on concentration of the analyte using the first value and the second value.

31 Claims, 7 Drawing Sheets

(56) References Cited

U.S. PATENT DOCUMENTS

| | | | |
|---|---|---|---|
| 2010/0312483 A1* | 12/2010 | Peyser | G01N 33/66 702/19 |
| 2011/0120206 A1* | 5/2011 | Troughton | A61B 5/1495 73/1.06 |
| 2012/0240656 A1 | 9/2012 | Crane | |
| 2013/0083820 A1 | 4/2013 | Barwell | |
| 2015/0198607 A1 | 7/2015 | Peyser | |
| 2020/0348275 A1* | 11/2020 | Mackenzie | G01N 1/22 |
| 2021/0121582 A1* | 4/2021 | Krishnamani | G01N 33/533 |

OTHER PUBLICATIONS

De Silva et al., Bright molecules with sense, logic, numeracy and utility, Org. Biomol. Chem., 2008:6:2468-2481.

Lee et al., Real-Time Observations of Intracellular Mg2+ Signaling and Waves in a Single Living Ventricular Myocyte Cell, Anal. Chem., 2009:81:538.

Martinez-Zaguila et al., Mag-Fura-2 (Furaptra) Exhibits both Low (μM) and High (nM) Affinity for Ca2+, Cell Physiol. Biochem., 1998:8:158.

Ge et al., "High-stability non-invasive autoclavable naked optical CO2 sensor", Biosensors and Bioelectronics, 15 2003:18:857-865.

Ge et al., "Study on low-cost calibration-free pH sensing with disposable optical sensors", Analytica Chimica 5 Acta, 2012:734:79-87.

Rovati et al, "Plastic Optical Fiber pH Sensor Using a Sol-Gel Sensing Matrix", Moh Yasin Sulaiman W. Harun and Hamzah AROF, eds. Fiber Optic Sensors.

Technical Compendium—CDI Blood Parameter Monitoring System 550—An overview of the CDI system 550 and its industry leading technology, Terumo Cardiovascular Systems Corporation, Oct. 2018.

Crane et al. "The Development of a Continuous Intravascular Glucose Monitoring Sensor", Journal of Diabetes Science and Technology, 2015:9:751-761.

Review on Recent Developments of Fluorescent Oxygen and Carbon Dioxide Optical Fiber Sensors, Photonic Sensors, 2011, 1, 234-250.

European Search Report completed on Sep. 15, 2020 for Application No. EP20165007.4.

International Search Report and Written Opinion regarding Application No. PCT/GB2021/050373 dated Apr. 21, 2021.

* cited by examiner

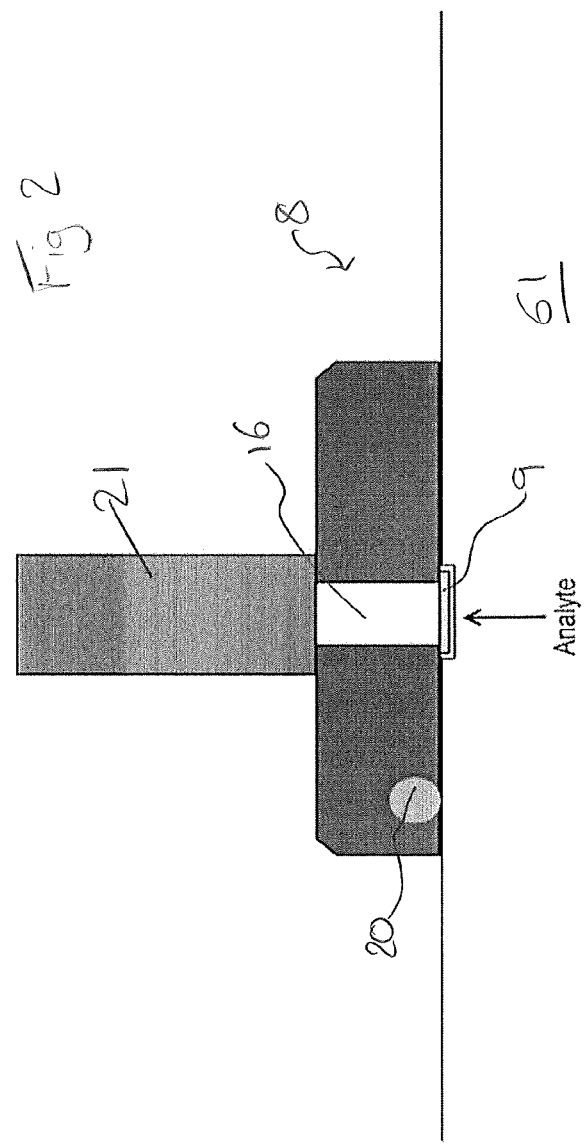

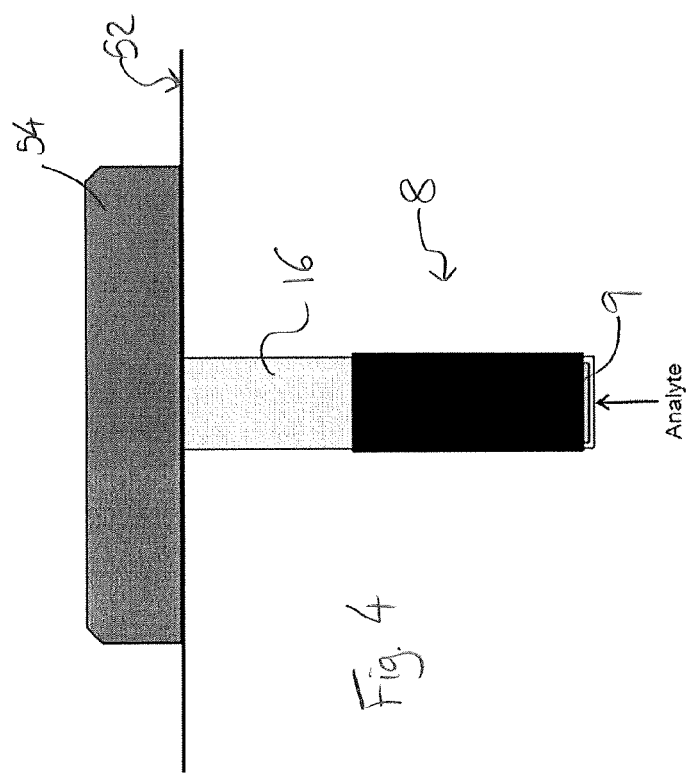
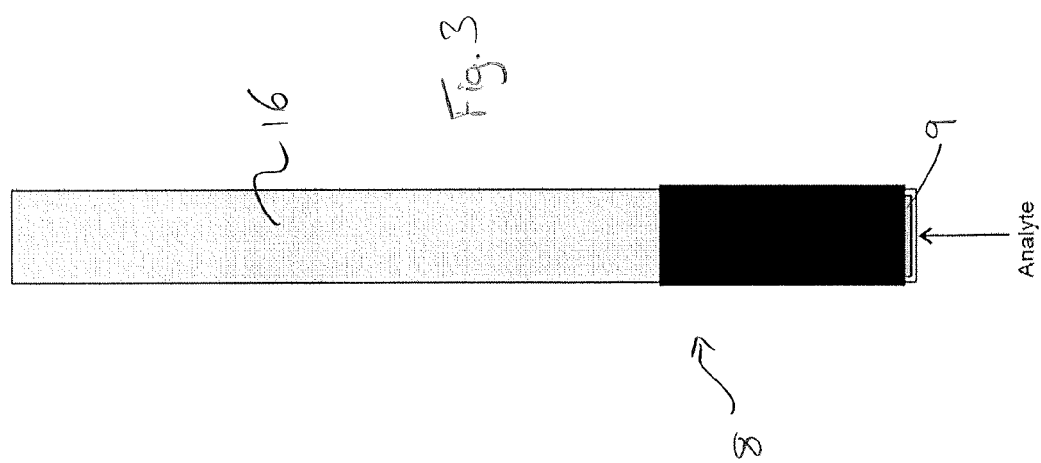

CALIBRATION OF A SENSOR

FIELD

The present application relates to methods for calibrating sensors comprising luminescent compounds, in particular calibration of sensors for detecting concentration of an analyte in an environment.

BACKGROUND

It is desirable in many areas to be able to determine the concentration of a particular analyte in an environment which may contain a mixture of several different substances. For example, in some clinical settings, such as dialysis treatment or monitoring of patients in intensive care, it is important to be able to accurately determine the concentration of carbon dioxide or ions such as potassium or sodium in a patient's blood in real time, and the provision of continuous real-time measurement data to a clinician in acute care settings is often invaluable as a means of guiding the administration of therapies. Another example is the monitoring of controlled environments in the food industry, where the presence of oxygen or other contaminants may be undesirable due to the risk of causing spoilage of food.

One known type of sensor uses a luminescent compound, for example a fluorescent organic dye, with a luminescence having a characteristic that depends on the concentration of the target analyte. By exciting the luminescent compound and measuring its luminescence while it is exposed to a sample containing the analyte, the concentration of the analyte in the sample can be determined. This type of sensor has the advantage that it can be operated continuously, so does not require taking regular samples, for example of blood or the atmosphere in which food is stored, for analysis or other similarly inconvenient procedures.

However, in order that the values of concentration reported by the sensors can be relied upon, it is necessary to calibrate the sensor to determine the dependence of the characteristic of the luminescence on the concentration of the analyte. Traditionally, calibration of luminescent sensors, for example for measuring concentrations of blood gases, have required complicated multi-point calibration procedures utilising specialised tonometric apparatus to provide controlled concentrations of particular analytes to calibrate the sensors. These apparatuses are complicated and expensive to maintain and operate, and the multi-point calibration procedures are often time-consuming. These factors mean that the process of calibrating the sensors consumes valuable user time, and creates substantial expense. The users may even forgo calibration entirely in time-pressured situations, leading to the potentially dangerous use of unreliable measurement values. Recent developments have reduced the size of such apparatuses and the number of calibration points needed, but a separate calibration apparatus and calibration procedure is still needed, which is expensive and time-consuming.

Therefore, there is a need for a calibration procedure for this type of sensor which reduces or eliminates the need for specialist calibration apparatus, and reduces the operator time needed to perform calibration. It is an object of the present invention to at least partially address this problem.

SUMMARY

There is provided a method of calibrating a sensor comprising a luminescent compound having a luminescence that depends on the concentration of an analyte, and a detector configured to detect light emitted by the luminescent compound, the method comprising providing a component comprising the luminescent compound in a package that maintains exposure of the luminescent compound to the analyte at a known first concentration, assembling the component into the sensor and measuring a first value of a characteristic of the luminescence of the luminescent compound while exposed to the analyte at the first concentration, measuring a second value of the characteristic of the luminescence of the luminescent compound while exposed to the analyte at a known second concentration different from the first concentration, and determining parameters representing the dependence of the characteristic of the luminescence on concentration of the analyte using the first value and the second value.

By providing the component of the sensor comprising the luminescent compound packaged such that it is exposed to a known concentration of the analyte, a first calibration point can be provided without requiring specialised equipment or any user preparation. This substantially reduces the time needed to calibrate the sensor, and removes the need for a separate apparatus to provide the first calibration point, thereby reducing the cost in time and resources to the user of operating the system.

In an embodiment, the step of assembling the component into the sensor is performed with the component retained in the package and the step of measuring the first value is performed while the component is in the package. The package may be designed such that the sensor can be connected while remaining in the package. The first calibration point can therefore simply be measured by connecting the component to the sensor (an operation that would already be performed by the user in existing systems) before removing it from the package.

In an embodiment, the step of measuring the first value is performed during a predetermined time period following the removal of the component from the package within which the luminescent compound remains exposed to the analyte at the first concentration. As an alternative, the design of the component and the properties of the luminescent compound may be such that the characteristic of the luminescence of the luminescent compound does not change substantially for a period of time after the component is removed from the packing. Therefore, the first calibration point can be measured by connecting the component to the sensor immediately after removing the component from the package (again an operation that would already have been performed by the user in existing systems). In an embodiment, the predetermined time period is at most 5 minutes. This is representative of embodiments of the component disclosed herein.

In an embodiment, the first concentration is zero. This is a particularly convenient, as it allows the characteristic in the absence of the analyte, a common calibration parameter, to be determined directly, rather than calculated from multiple measurements.

In an embodiment, the step of measuring a second value is performed while the luminescent compound is exposed to blood containing the analyte at the second concentration. This is a convenient choice of measurement for the second value where the sensor is to be used to measure the concentration of analytes in blood, because it can be performed after setting up the sensor in the configuration in which it is to be used. Therefore, the disruption required for calibration purposes is minimized, because the user can simply assemble the sensor and setup the apparatus for use, and calibration measurements are taken automatically at the appropriate stages of the setup procedure.

In an embodiment, the second concentration is determined by analysis of a sample of the blood using a blood analyser. Blood analysers are commonly present in clinical settings for analysis of patient samples. Therefore, no additional equipment is required to determine the second concentration for the purposes of calibration.

In an embodiment, the step of measuring a second value is performed in vivo. As discussed above, this is particularly advantageous because it means that no additional setup steps are needed before or after measuring the second value.

In an embodiment, the step of measuring a second value is performed while the luminescent compound is exposed to a pre-prepared fluid containing the analyte at the known second concentration. Using a pre-prepared fluid may be more convenient in some situations, because it provides a known second concentration without any additional analysis.

In an embodiment, the method further comprises assembling the sensor into a flow line for biological fluids in a medical device, wherein the pre-prepared fluid is a priming fluid for use in setup of the medical device. In some clinical situations, for example dialysis, a priming fluid is used during setup. Using this priming fluid to provide the second concentration further integrates the calibration into method steps that would anyway be performed by the user, thereby reducing the additional time needed to perform calibration.

In an embodiment, the luminescence depends on the temperature of the luminescent compound, and the parameters represent the dependence of the characteristic of the luminescence on both the concentration of the analyte and the temperature of the luminescent compound. Accounting for temperature variation that may occur during monitoring improves the accuracy and reliability of the calibration procedure.

In an embodiment, the method further comprises measuring a first temperature of the luminescent compound when the step of measuring the first value is performed, and measuring a second temperature of the luminescent compound when the step of measuring the second value is performed, and wherein the step of determining parameters representing the dependence of the characteristic of the luminescence on concentration of the analyte uses the first temperature and the second temperature in addition to the first value and the second value. Measuring the temperatures at the two calibration points can allow the calibration parameters to be adjusted for any difference between the temperatures at the two concentrations that may affect the characteristic of the luminescence, thereby further improving accuracy and reliability.

In an embodiment, the parameters include a temperature parameter representing the dependence of the characteristic of the luminescence on the temperature of the luminescent compound. Using a specific temperature parameter means that the temperature dependence can be easily quantified and accounted for.

In an embodiment, the temperature parameter has a predetermined value. In some embodiments, the behaviour of components is sufficiently consistent that the temperature parameter can be determined during manufacture. This removes the need for a temperature parameter to be determined during calibration, thereby reducing the complexity of the calibration.

In an embodiment, the method further comprises measuring a third value of the characteristic of the luminescence of the luminescent compound while the luminescent compound is exposed to the analyte at the first concentration at a third temperature different from the first temperature, and measuring the third temperature of the luminescent compound when the step of measuring the third value is performed, and wherein the step of determining parameters representing the dependence of the characteristic of the luminescence on concentration of the analyte uses the third value and the third temperature, in addition to the first value, the second value, the first temperature and the second temperature. Measuring the value of the characteristic at two temperatures at the first concentration allows the temperature parameter to be determined exactly if it is not possible to rely on a predetermined value. This still does not require additional steps from the user, because the measurements can be performed automatically after assembly of the component into the sensor.

In an embodiment, the luminescence depends on the temperature of the luminescent compound, and the parameters represent the dependence of the characteristic of the luminescence on the concentration of the analyte at a predetermined temperature. Where the temperature of the calibration measurements and the measurements during operation will be sufficiently similar, there is no need for additional measurements or parameters to quantify the temperature dependence.

In an embodiment, the characteristic of the luminescence of the luminescent compound is the intensity of the luminescence. Intensity is a convenient choice of characteristic that can be directly measured using a light detector.

In an embodiment, the characteristic of the luminescence of the luminescent compound is a ratio of the intensity of the luminescence at two different wavelengths. Using a ratio of intensity is advantageous because it reduces the sensitivity of the measurements to certain types of error.

In an embodiment, the dependence of the characteristic is modelled using a one to one host-guest binding model. This model is appropriate for modelling many commonly-available luminescent compounds.

In an embodiment, determining parameters representing the dependence comprises using a predetermined value for the strength of association between the luminescent compound and the analyte. This strength of association of the interaction is called the association constant. The association constant is generally consistent between components, and can therefore be determined during manufacture, and a predetermined value used at point of use.

In an embodiment, the dependence of the characteristic C on the concentration [X] of the analyte is modelled using the following equation:

$$C = \frac{C_0 + [X]KC_\infty}{1 + [X]K}$$

wherein $C_0$ is a value of the characteristic of the luminescence of the luminescent compound when the concentration of the analyte is zero, $C_\infty$ is a value of the characteristic of the luminescence of the luminescent compound when the concentration of the analyte is infinite, K is the strength of association between the luminescent compound and the analyte (the association constant), and determining parameters representing the dependence comprises determining $C_0$ and $C_\infty$. This is a convenient and appropriate specific choice of mathematical form to express the one-to-one host-guest binding model.

In an embodiment, the parameters include a temperature parameter α representing the dependence of the characteristic of the luminescence on the temperature of the luminescent compound, and $C_0$ and $C_\infty$ are modelled using the following dependence on the temperature T:

$$C_0(T)=C_{0c}(1+\alpha(T-T_c))$$

$$C_\infty(T)=C_{\infty c}(1+\alpha(T-T_c))$$

wherein $C_{0c}$ is the value of $C_0$ at temperature $T_c$, and $C_{\infty c}$ is the value of $C_\infty$ at temperature $T_c$. Using a linear dependence of the characteristic of luminescence on temperature is sufficiently accurate over the range of temperatures in which sensors of this type are commonly used. It is therefore a favourable choice as a simple and effective model.

In an embodiment, K is modelled using the following dependence on the temperature T:

$$K(T) = K_c \exp\left(\beta\left(1 - \frac{T_c}{T}\right)\right)$$

wherein $K_c$ is the association constant at temperature $T_c$ and $\beta$ is an association temperature constant. An exponential dependence of the association constant accurately reflects its temperature dependence in the conditions the sensor is generally used.

There is further provided a method of measuring a concentration of an analyte in a sample using a sensor comprising a luminescent compound having a luminescence that depends on the concentration of the analyte, and a detector configured to detect light emitted by the luminescent compound, the method comprising calibrating the sensor using an embodiment of the method of calibrating the sensor disclosed above, measuring a value of the characteristic of the luminescence of the luminescent compound while exposed to the sample, deriving the concentration of the analyte in the sample using the measured value and the determined parameters representing the dependence of the characteristic of the luminescence on concentration of the analyte. Providing a method of measuring concentration that uses the previously-described calibration method is advantageous because it will provide accurate measurements of the concentration with reduced burden on the user during setup of the sensor.

In an embodiment, the sample is a biological fluid, and the value of the characteristic of the luminescence is measured in vivo. Measurement in vivo can allow for continuous monitoring, rather than having to take regular blood samples for analysis. This provides greater time resolution of monitoring without requiring a clinician to spend time taking regular samples.

In an embodiment, the sample is a biological fluid, and the value of the characteristic of the luminescence is measured in vitro. This may be more convenient in situations such as dialysis treatment, where biological fluids are being continuously circulated and are available for measuring in vitro. For example, in an embodiment, the method further comprises assembling the sensor into a flow line for biological fluids in a medical device, wherein the sample is present in the flow line.

In an embodiment, the biological fluid is blood or interstitial fluid. These are both suitable samples for measuring the level of important metabolites in the body, and so are advantageous choices when monitoring patient health.

In an embodiment of either method, the component is a replaceable component of the sensor. This is advantageous for maintaining sterility when the component is used in clinical contexts.

In an embodiment of either method, the sensor further comprises a light source configured to excite the luminescent compound, and measuring a value of the characteristic of the luminescence of the luminescent compound comprises exciting the luminescent compound using the light source, and detecting light emitted by the luminescent compound using the detector. This allows for greater control over the measurement process by controlling the light delivered to the luminescent compound. This improves the accuracy of lifetime measurements used to derive concentrations.

In an embodiment of either method, the analyte is one of carbon dioxide, hydrogen ions, sodium, potassium, magnesium, and calcium. Accurate calibration of carbon dioxide or oxygen sensors is important for ensuring that patients do not become hypoxic during clinical procedures. Other metabolites are also important targets for measurement in intensive care to ensure patient health.

In an embodiment of either method, the luminescent compound comprises a fluorescent compound. Fluorescent compounds emit light at higher intensity than phosphorescent compounds, and so are more easily detected. In an embodiment, the fluorescent compound comprises 8-hydroxypyrene-1,3,6-trisulfonic acid. This is a particularly suitable choice of fluorescent compound for sensing carbon dioxide or pH.

DRAWINGS

Embodiments of the present invention will now be described by way of non-limitative example with reference to the accompanying drawings, in which:

FIG. 2 is a schematic of a possible configuration of a sensor probe for extracorporeal measurement of analyte concentration in blood;

FIG. 3 is a schematic of a possible configuration of a sensor probe for intravascular measurement of analyte concentration in blood;

FIG. 4 is a schematic of a possible configuration of a sensor probe for subcutaneous measurement of analyte concentration in blood;

DETAILED DESCRIPTION OF EMBODIMENTS

Figure 1:
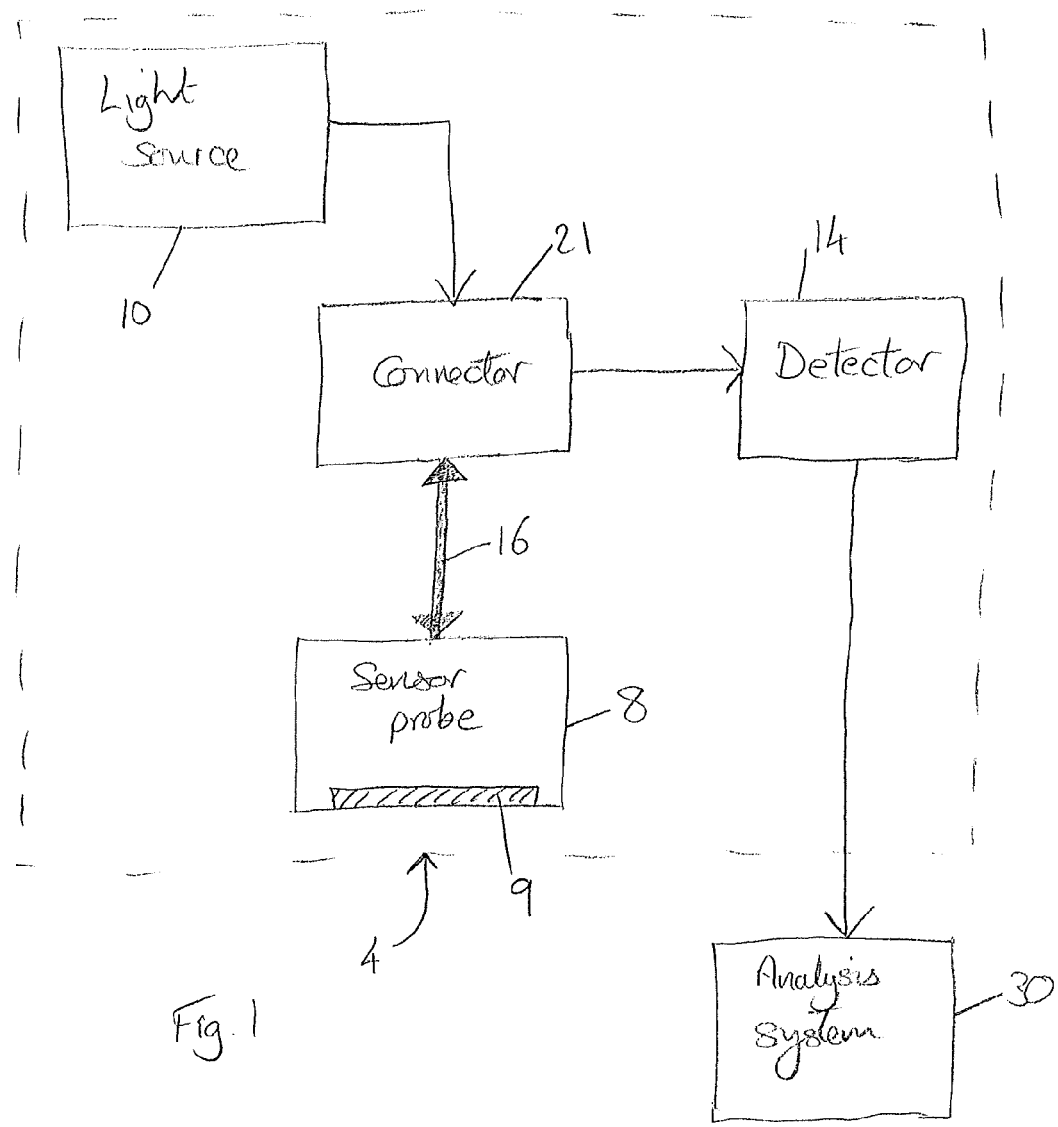
FIG. 1 is a schematic of a sensor apparatus in which the present invention may be implemented.

The present disclosure provides a method of calibrating a sensor. FIG. 1 shows a sensor apparatus comprising a sensor 4 of the type for which the methods disclosed herein could be used. An example of such a sensor 4 may be a pH sensor for sensing carbon dioxide concentrations. The sensor 4 comprises the luminescent compound 9, and an analysis system 30.

The sensor 4 comprises a light source 10 configured to excite the luminescent compound. The light source 10 is configured to emit light that at appropriate wavelengths to excite the luminescent compound 9. For example, the light source 10 may be any light source capable of emitting light at the wavelengths and intensities required to excite the luminescent compound 9. For example, the light source 10 may comprise a laser diode or an LED. The light source 10 may be a continuous light source, a light source with oscillating intensity, or a pulsed light source.

The sensor 4 further comprises a detector 14 configured to detect light emitted by the luminescent compound 9. The detector 14 may be any device capable of producing a signal in response to receiving light at the wavelengths emitted by the luminescent compound 9. For example, the detector 14 may comprise a charge-coupled device, an active-pixel sensor, a photodiode, or photoresistor. The signal output by the detector 14 may represent the intensity of light received from the luminescent compound 9.

The sensor 4 comprises an optical fibre 16, arranged to guide light to and from the luminescent compound 9. Optical fibres use total internal reflection to prevent light being lost from the fibre. This means light can be efficiently carried to and from the luminescent compound 9, improving the signal and providing for higher-quality and more reliable measurements. They can also be made small and flexible, so are particularly suitable for sensors that must be inserted into the body of a patient. For example, the optical fibre 16 may comprise a PMMA fibre optic. The optical fibre 16 functions as an optical waveguide and any other suitable optical waveguide may be used in place of the optical fibre 16, when appropriate.

A component is provided comprising the luminescent compound 9, the component being assembled into the sensor 4. In FIG. 1, the component is a sensor probe 8 comprising the luminescent compound 9. The component is exposed to a sample containing the analyte during operation of the sensor apparatus. In an embodiment, the sample comprises blood. The sensor 4 further comprises a connector 21 configured to connect the sensor probe 8 to the light source 10 and the detector 14. In an embodiment, the component is a replaceable component of the sensor 4. Some or all of the sensor 4 may be disposable, in particular the replaceable component may be disposable. This is convenient in clinical contexts, where the sensor 4 is used to measure analyte concentrations inside the body of a patient. In such cases, the part of the sensor 4 which is inserted into the patient must be sterile and cannot be reused between patients. For example, only the sensor probe 8 comprising the luminescent compound 9 may be disposable and not the detector 14 or light source 10.

The analysis system 30 is configured to carry out the method by controlling the sensor 4 and performing processing of signals received from the detector 14. The analysis system 30 may also be configured to calibrate the sensor, and/or derive a measure of concentration of the analyte based on measurements from the sensor 4. The analysis system 30 may be connected to the sensor 4 via a wired connection, for example a serial or Ethernet connection, or another interface type specifically designed for the sensor apparatus. Alternatively a wireless connection, such as BLUETOOTH® or Wi-Fi may be used. The analysis system receives signals output by the detector 14, and may also transmit signals to the sensor 4, for example to control the light source 10.

FIGS. 2 to 4 show specific example embodiments of the sensor 4 for use in clinical contexts and in the case that the sensor 4 comprises a sensor probe 8.

FIG. 2 shows an embodiment in which the sensor 4 is a bypass sensor. Such sensors could be used in an external blood pump to monitor concentrations of analytes in the blood being pumped. Measurements of analyte concentration, in particular oxygen or carbon dioxide, may be used as part of the control of a blood pumping rate by the external blood pump, for example to maintain appropriate levels of oxygenation of blood. In this case, the component is a disposable sensor probe 8 mounted on a bypass loop 61 such that the luminescent compound 9 is exposed to blood passing through the bypass loop. The connector 21 connects the disposable sensor probe 8 to the remainder of the sensor 4. A thermistor or another suitable temperature sensor 20 is mounted within the sensor probe 8 to measure the temperature of the blood.

FIG. 3 shows an embodiment in which the sensor 4 is an intravascular sensor. The luminescent compound 9 is located on the tip of the optical fibre 16 that is inserted into the patient via a catheter. The component is a sensor probe 8 containing the fibre optic 16 along with a temperature sensor 20. The sensor probe 8 is connected to the rest of the sensor 4 via the connector 21.

FIG. 4 shows an embodiment in which the sensor 4 is an interstitial sensor. In this case the sensor 4 comprises the component, which comprises a sensor probe 8, and an outer part 54. The sensor probe 8 punctures the skin 52 and measures analyte concentrations in interstitial fluid. A retractable needle may be used to puncture the skin 52 and the sensor 4 is connected to the analysis system 30 wirelessly. Alternatively, the analysis system 30 may be disposed in the outer part 54. A temperature sensor is provided to measure the skin temperature. This may be provided within the sensor probe 8 which penetrates the skin 52, or in proximity to the skin 52 within the outer part 54.

The luminescent compound 9 may be any suitable substance having a luminescence that depend on the concentration of the analyte. The luminescent compound 9 may be provided in the sensor probe 8 immobilised in a polymeric layer.

In some embodiments, the characteristic of the luminescence that is measured in the method may be the luminescence emission intensity (such as the fluorescence emission intensity or the phosphorescence emission intensity). Alternatively, the characteristic of the luminescence may be the luminescence lifetime (such as the fluorescence lifetime or the phosphorescence lifetime).

In applications where the amount of luminescent compound 9 is small, it can be difficult to detect absorption by the luminescent compound 9 against the background of excitation light. It is therefore preferred that the luminescent compound emits light over a range of wavelengths different to the range of wavelengths over which the luminescent compound is excited, as this makes distinguishing between the excitation light and the light emitted from the luminescent compound 9 easier.

The luminescence may be fluorescence or phosphorescence. However, phosphorescence is typically weaker than fluorescence as it involves a spin-forbidden transition. In order to provide a luminescent compound 9 with a strong optical response to excitation light, it is therefore preferred that the luminescent compound 9 is a fluorescent compound with a fluorescence that varies when the luminescent compound interacts with an analyte.

Accordingly, it is preferred that the luminescent compound 9 comprises a fluorophore. A fluorophore is a moiety which can absorb light and re-emit light by fluorescent emission. Usually, the fluorophore absorbs light in the visible region of the electromagnetic spectrum. The fluorophore also usually emits light in the visible region of the electromagnetic spectrum. By "the visible region of the electromagnetic spectrum" is meant electromagnetic radiation having a wavelength of from about 400 nm to about 700 nm. The fluorophore may also absorb and/or emit radiation outside the visible region of the electromagnetic spectrum. In a preferred embodiment, therefore, the luminescent compound 9 is a luminescent compound comprising a fluorophore, and the fluorescence emission spectrum of the fluorophore varies in the presence of the analyte.

Variation in a characteristic of the luminescence (such as the emission spectrum of the luminescent compound) is induced by interaction with an analyte. Possible modes of interaction between the analyte and the luminescent compound include:

ionic interactions;

formation of reversible covalent interactions (i.e. the formation of boronic esters);

any other non-covalent interaction leading to a 1:1 host-guest complex, i.e. hydrogen bonding, CH-π interactions, hydrophobic effects, Van der Waals interactions, etc.

Other modes of interaction are possible. These interactions will alter one or more characteristics of the luminescence, which may be optically detected.

In some cases, as where the interaction between analyte and luminescent compound involves collisional quenching of the luminescent compound, the analyte does not bind to the luminescent compound. However, in other cases, a chemical bond such as an ionic bond or a covalent bond may be formed between the analyte and the luminescent compound. In such cases, the luminescent compound may comprise a receptor moiety. A receptor moiety is a moiety which can bind to an analyte. It may be preferred that the luminescent compound comprises a receptor moiety, as a receptor moiety typically binds preferentially to the analyte and not to other chemical species. Thus, a luminescent compound comprising a receptor moiety typically generates an optical signal associated specifically with the analyte, which has low susceptibility to interference from other species. A number of examples of luminescent compounds that could be used for different analytes are provided below for illustrative purposes only.

In an example, the luminescent compound may comprise a moiety of formula (I):

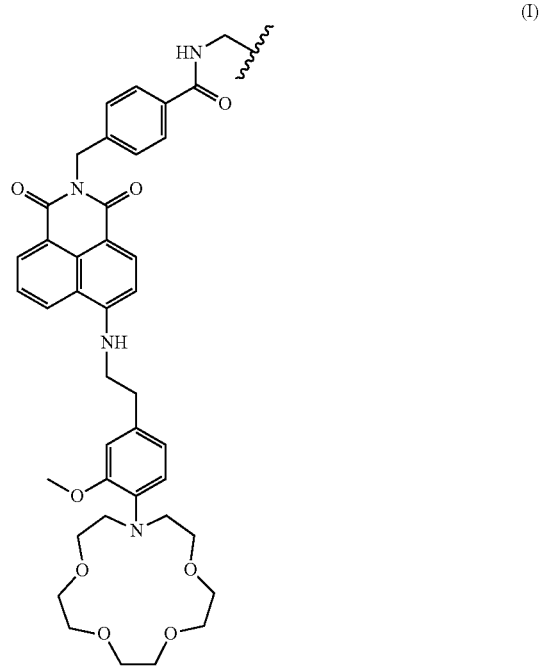 [SMILES: *CNC(=O)c1ccc(CN2C(=O)c3cccc4c(NCCc5ccc(N6CCOCCOCCOCCOCC6)c(OC)c5)ccc(c34)C2=O)cc1]

(I)

or a derivative thereof. The wavy line indicates the point of attachment to another moiety; this may be, for example, the polymer of the polymeric layer or an organic moiety such as an alkyl group. The species of formula (I) comprises both a receptor (the cryptand, which can bind $Na^+$) and a fluorophore comprising the polycyclic aryl moiety. When $Na^+$ binds to the cryptand, the fluorescent emission of this moiety alters.

In another example, the luminescent compound may comprise a moiety of formula (II):

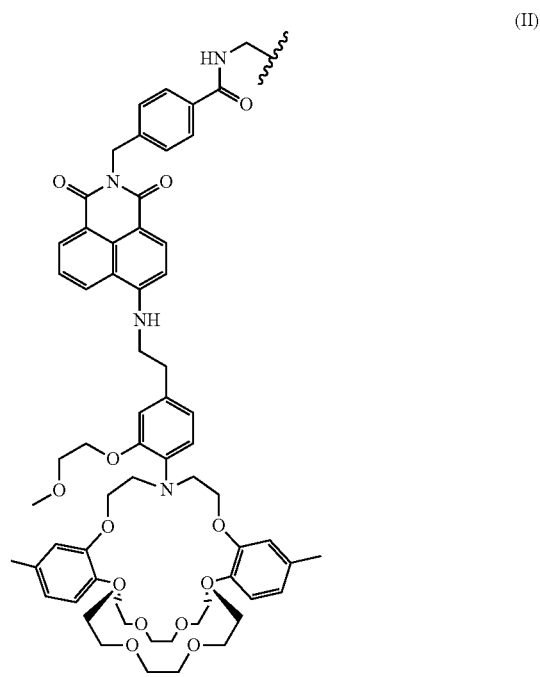

(II)

or a derivative thereof. The wavy line indicates the point of attachment to another moiety; this may be, for example, the polymer of the polymeric layer or an organic moiety such as an alkyl group. The species of formula (II) comprises both a receptor (the cryptand, which can bind $K^+$) and a fluorophore comprising the polycyclic aryl moiety. When $K^+$ binds to the cryptand, the fluorescent emission of this moiety alters.

In another example, the luminescent compound may comprise a moiety of formula (III):

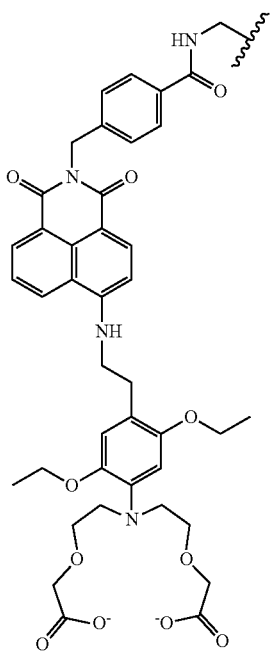

(III)

or a derivative thereof. See, for instance, Tusa & He, J. Mater. Chem., 2005:15:2640-2647; de Silva et al., Org. Biomol. Chem., 2008:6:2468-2481. The wavy line indicates the point of attachment to another moiety; this may be, for example, the polymer of the polymeric layer or an organic moiety such as an alkyl group. The species of formula (III) comprises both a receptor (the moiety including the pair of carboxylate ions which can bind $Ca^{2+}$) and a fluorophore comprising the polycyclic aryl moiety. When $Ca^{2+}$ binds to the receptor, the fluorescent emission of this moiety alters.

In another example, the luminescent compound may comprise a moiety of formula (IV) or (V):

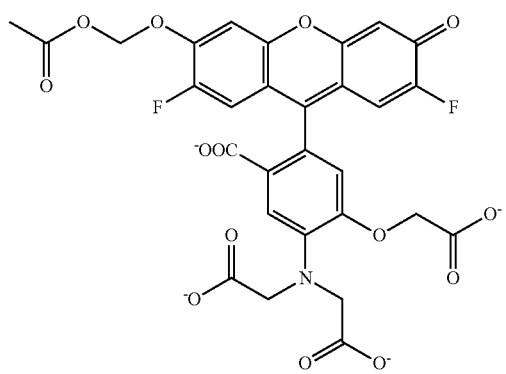

or a derivative thereof. See, for instance, Lee et al., Anal. Chem., 2009:81:538 or Martinez-Zaguila et al., Cell Physiol. Biochem., 1998:8:158. The moiety of formula (IV) or (V) may be attached at any point to the polymer comprised in the polymeric layer. These compounds are known as Mag-fluo-4 (compound (IV)) and Mag-fura-2 (compound (V)) respectively. The species of formula (IV) and (V) bind to $Mg^{2+}$ ions via the methyl ester moieties. Compound (V) is therefore an example of a luminescent compound comprising more than one receptor. These compounds also comprise a fluorophore comprising a polycyclic aryl moiety. When $Mg^{2+}$ binds to either of these compounds, their fluorescent emission alters.

In another example, the luminescent compound may comprise a moiety of formula (VI):

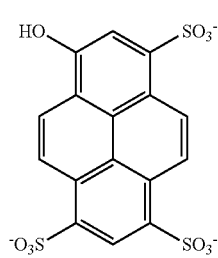

(VI)

That is, pyranine, or a derivative thereof. See for instance Ge et al., "High-stability non-invasive autoclavable naked optical CO2 sensor", Biosensors and Bioelectronics, 2003: 18:857-865. This moiety may be attached at any point except the hydroxyl group to the polymer of the polymeric layer. The compound of formula (VI) does not comprise a separate receptor and fluorophore; the fluorophore itself acts as the receptor. The moiety of formula (VI) can be used to detect acid or $CO_2$, because $CO_2$ forms an acid (carbonic acid) in the presence of water. In the presence of acid (such as carbonic acid formed by $CO_2$), the hydroxyl group of the moiety of formula (VI) is protonated. However, as the concentration of acid or $CO_2$ decreases, the hydroxyl moiety becomes deprotonated, leaving a negative charge which is delocalised throughout the fluorophore, changing the fluorescence emission spectrum, and the fluorescence absorption spectrum, of the compound. This change is particularly promoted where the luminescent compound comprising a moiety of formula (VI) is immobilised in the polymeric matrix together with a phase transfer agent. An exemplary phase transfer agent is hexadecyltrimethylammonium hydroxide.

A suitable derivative of pyranine which may be used is a moiety of formula (VII), below.

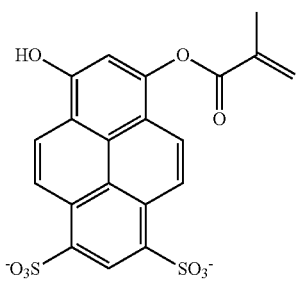

(VII)

See for instance Ge et al., "Study on low-cost calibration-free pH sensing with disposable optical sensors", Analytica Chimica Acta, 2012:734:79-87.

In another example, the luminescent compound may comprise a moiety of formula (VIII):

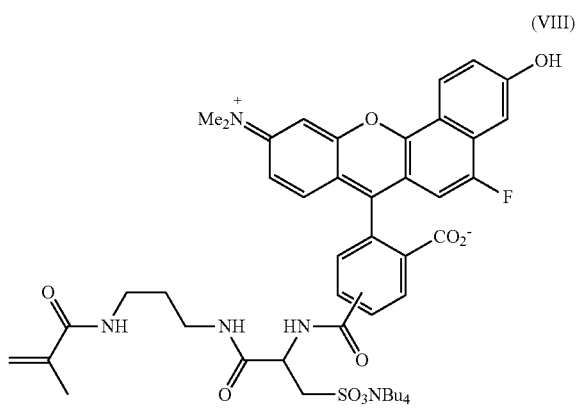

(VIII)

or a derivative thereof. This moiety may be attached at any point to the polymer of the polymeric layer. The compound of formula (VIII) behaves in a similar way to the moieties of formula (VI) and (VII): it does not comprise a separate receptor and fluorophore; the fluorophore itself acts as the receptor. In the presence of acid (such as carbonic acid formed by $CO_2$), the hydroxyl group of the moiety of formula (VIII) is protonated. However, as the concentration of acid or $CO_2$ decreases, the hydroxyl moiety becomes deprotonated, leaving a negative charge which is delocalised throughout the fluorophore, changing the fluorescence emission spectrum, and the fluorescence absorption spectrum, of the compound.

Other luminescent compounds are known, and in many cases are commercially available; these compounds may also be used as a luminescent compound. In some embodiments, the luminescent compound comprises 8-Hydroxypyrene-1,3,6-trisulfonic acid (HPTS). A yet further example of a luminescent compound which can be used to detect acid or $CO_2$ is:

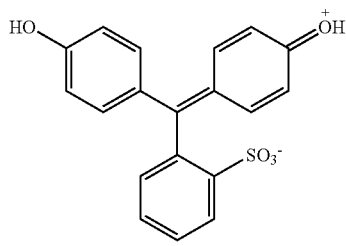

See for example Rovati et al, "Plastic Optical Fiber pH Sensor Using a Sol-Gel Sensing Matrix", MOH. YASIN Sulaiman W. Harun and Hamzah AROF, eds. Fiber Optic Sensors.

It will be clear from the above that the sensor may be used for the optical sensing of a wide variety of analytes. The analyte may be, for example, an ion, a gas, an inorganic compound or an organic compound. The analyte may be present in the sample as a gas, or alternatively it may be dissolved or suspended in another substance, for example a liquid such as interstitial fluid or blood. Where the analyte is an organic compound, it is typically a small organic compound, for example an organic compound comprising fewer than 20 carbon atoms. Particular examples of small organic compounds include saccharides, sugar alcohols, and metabolites such as urea or ketones. Particularly preferred examples of the analyte are $Na^+$, $K^+$, $Ca^{2+}$, $Mg^{2+}$, $CO_2$, and acid ($H^+$, i.e. a pH sensor). In an embodiment, the analyte is carbon dioxide.

Figure 5:
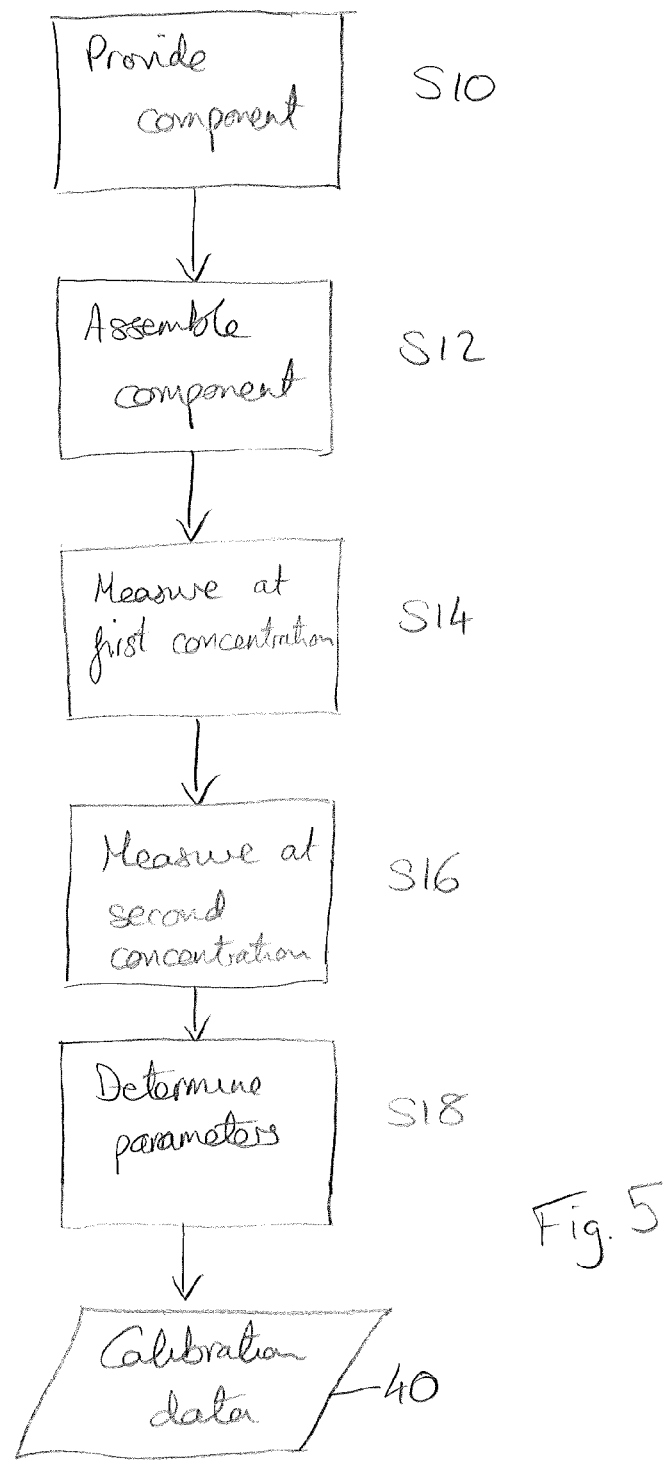
FIG. 5 is a flowchart of a method of calibrating a sensor of the sensor apparatus shown in FIG. 1.

FIG. 5 shows a flowchart of an embodiment of the method of calibrating the sensor of FIG. 1.

Figure 6:
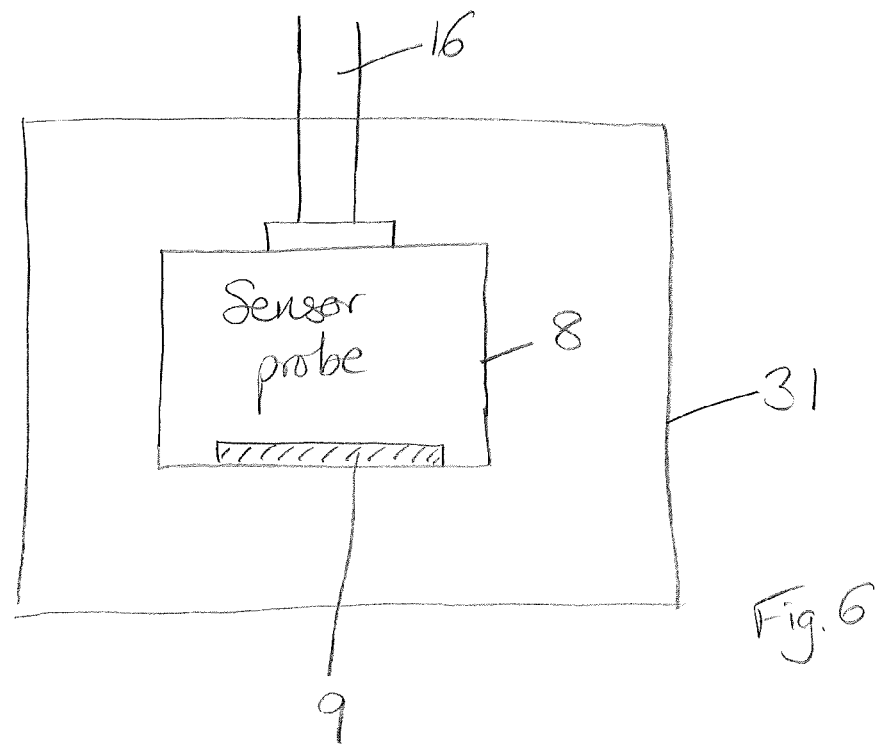
FIG. 6 is a schematic of a component packaged so the first value can be measured while sealed in the package.
Figure 7:
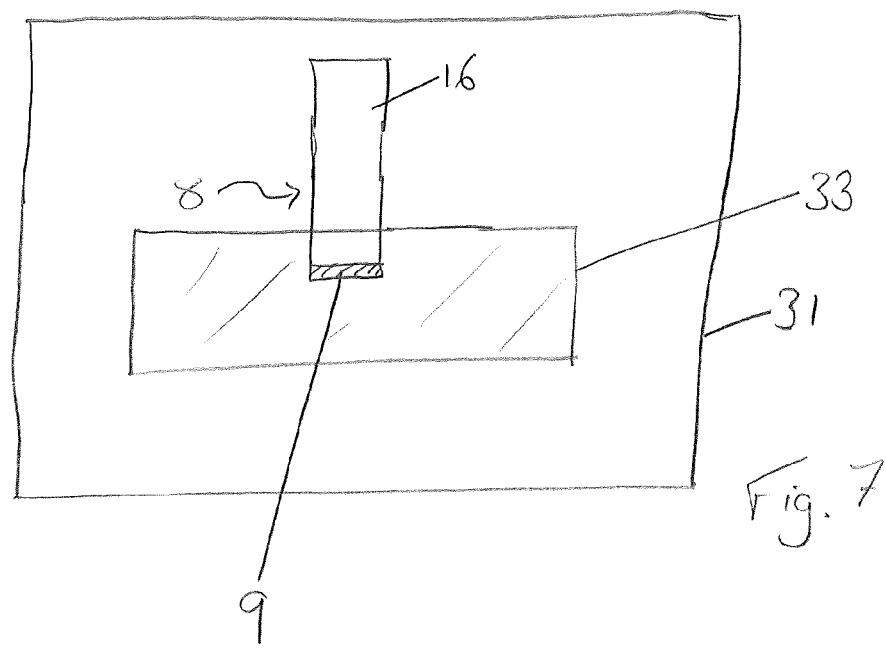
FIG. 7 is a schematic of a component designed and packaged so the first value can be measured after the component is removed from the package.

In step S10, the method comprises providing a component comprising the luminescent compound 9 in a package 31 that maintains exposure of the luminescent compound 9 to the analyte at a known first concentration. In FIG. 1, the component is a sensor probe 8. Examples of packages 31 are shown in FIGS. 6 and 7. By providing the component in the package 31, a known first concentration of analyte is provided in the package 31 to be used as a first calibration point during the calibration method. The first concentration can be controlled during manufacture of the components, and so there is no need for the user to have to provide this first concentration, for example by operating specific calibration equipment such as required in prior art devices. In an embodiment, the first concentration is zero. As will be discussed further below, the value of the characteristic at zero concentration may be directly a parameter of the dependence of the characteristic on concentration of the analyte. Therefore, having zero concentration as one of the values used for calibration simplifies the determination of parameters of the dependence.

In step S12, the method comprises assembling the component into the sensor 4. In FIG. 1, this comprises connecting the component to the connector 21 of the sensor 4. Assembling the component into the sensor 4 allows the sensor 4 to excite the luminescent compound 9 and detect light emitted by the luminescent compound 9, thereby allowing measurements to be made to calibrate the sensor 4.

In step S14, the method comprises measuring a first value of the characteristic of the luminescence of the luminescent compound 9 while exposed to the analyte at the first concentration. The first concentration provides the first known concentration of analyte for calibrating the sensor 4. By determining the value of the characteristic at the first concentration, the analysis system 30 can extrapolate to determine the concentration at other concentrations based on other measurements of the value of the characteristic. This will be discussed in more detail below. The sensor 4 of FIG. 1 comprises a light source 10 configured to excite the luminescent compound 9. Step S14 comprises exciting the luminescent compound 9 using the light source 10, and detecting light emitted by the luminescent compound 9 using the detector 14.

In an embodiment, the package 31 is that of FIG. 6, step S12 is performed with the component retained in the package 31, and step S14 is performed while the component is in the package 31. This allows the exposure of the luminescent compound 9 to the known first concentration to be maintained while the first value is measured. This embodiment requires the package 31 to be designed such that the component can be connected to the sensor 4 without unsealing the package 31. In FIG. 6, a portion of the fibre optic 16 of the component protrudes from the package 31, with the package 31 sealed around the fibre optic 16. Alternatively an adaptor may be provided as part of the package 31, with the package 31 sealed around the adaptor, wherein the adaptor is connected to the component inside the package 31, and is configured to be connected to the connector 21 of the sensor 4 in step S12.

In an embodiment, the package 31 is that of FIG. 7, and step S4 is performed during a predetermined time period following the removal of the component from the package 31 within which the luminescent compound 9 remains exposed to the analyte at the first concentration. Depending on the choice of luminescent compound 9 and the design of the component, the characteristic of the luminescence may not change rapidly on removal of the component from the package 31. Therefore, a time period may exist in which the first value can be measured while the luminescent compound 9 remains exposed to the analyte at the first concentration. In FIG. 7, the component is a bypass sensor probe 8 similar to that shown in FIG. 2, and comprises a section of tubing 33 to be connected into a bypass loop of, for example, a dialysis system. The tubing 33 is pre-filled with fluid containing the analyte at the first concentration. It will take some time for the concentration of analyte in the fluid to change following removal of the component from the package 31, and therefore during this period, step S14 can be performed. In an embodiment, the predetermined time period is at most 5 minutes, preferably at most 3 minutes, more preferably at most 1 minute.

The characteristic of the luminescence may be one of a number of characteristics. For example, the characteristic may be a lifetime of the luminescence.

In an embodiment, the characteristic of the luminescence of the luminescent compound 9 is the intensity of the luminescence. When the characteristic of the luminescence is intensity, step S14 comprises exciting the luminescent compound 9 using light of a first wavelength, and measuring the intensity of light emitted at a second wavelength. The first wavelength may be chosen to be a wavelength at which the luminescent compound 9 has a maximum absorption of light. The second wavelength may be the wavelength at which the intensity of emitted light is greatest, or where the emission spectrum of the luminescent compound 9 has a maximum. The specific excitation and detection wavelengths will depend on the choice of luminescent compound 9.

In an embodiment, the characteristic of the luminescence of the luminescent compound 9 is a ratio of the intensity of the luminescence at two different wavelengths. Using the ratio of the intensity at two different wavelengths may be advantageous in reducing or eliminating the effects of certain types of error on the measured values of the characteristic. In this case, the values of the characteristic of the luminescence may be measured in different ways, depending in part on the choice of luminescent compound 9. As described above, the luminescent compound 9 is preferably a fluorescent compound. Sensors 4, for example comprising a fibre optic 16 as described above, have been developed with fluorescent compounds that have a single absorption peak that, when excited with light of a single wavelength, give two overlapping emission peaks.

In an embodiment where the characteristic of the luminescence is a ratio of the intensity of the luminescence at two different wavelengths, step S14 comprises exciting the luminescent compound 9 using light of a first wavelength, and measuring the intensity of light emitted at each of the two different wavelengths, wherein the first wavelength is the same for each of the two different wavelengths. This implementation may be preferred in some situations, because only light of a single wavelength is necessary to produce the two overlapping peaks in the emission spectrum. This reduces the complexity of the light source 10, and additionally any variation in the output from the light source 10 will affect both emission peaks equally. This allows the variation to be effectively removed as an error by the calculation of the ratio. However, this will require the detector 14 to be able to distinguish between light at different wavelengths.

For other luminescent compounds, such as HPTS, excitation at different wavelengths results in a single emission peak. For example, the signal from exciting HPTS at 405 nm, 470 nm, and 418 nm results in a single fluorescent emission at 525 nm. FIG. 7 shows the absorption spectra of a sensor 4 comprising HPTS with increasing carbon dioxide concentrations, where the arrows indicate the peak movements with increasing carbon dioxide concentrations. In such an embodiment where the characteristic of the luminescence is a ratio of the intensity of the luminescence at two different wavelengths, step S14 comprises for each of the two different wavelengths, exciting the luminescent compound 9 using light at the one of the two different wavelengths, and measuring the intensity of light emitted by the luminescent compound 9 at a second wavelength, wherein the second wavelength is the same for each of the two different wavelengths. This may be preferred where the detector 14 is only able to detect intensity of light, and not wavelength, but will require the light source 10 to be able to emit light at two different wavelengths.

Performing step S14 while the component is in the package 31, or shortly after removing the component from the package 31, has the advantage that one of the measurements needed for calibration is measured in a part of the setup of the sensor 4 that would have to be performed even if no calibration took place (i.e. steps S10 and S12). This saves the user time, because they are not required to operate additional equipment or perform additional actions to obtain the first calibration value.

In step S16, the method comprises measuring a second value of the characteristic of the luminescence of the luminescent compound 9 while exposed to the analyte at a known second concentration different from the first concentration. The dependence of the characteristic of the luminescent compound 9 on the concentration of the analyte is such that at least two calibration measurements are needed in order to properly calibrate the sensor 4 to provide reliable measures of concentration during operation. It is preferred that the second value is also measured during a step that would be performed as part of the setup of the sensor 4 even if no calibration were required.

In some embodiments, step S16 is performed while the luminescent compound 9 is exposed to blood containing the analyte at the second concentration. In many cases, the sensor 4 is used to measure the concentration of analytes in blood, and in these cases the sensor 4 must be set up to be exposed to the blood of a patient. Using the concentration of the analyte in blood to determine the second value therefore also does not require placing the sensor 4 into any specialised calibration equipment. In an embodiment, the second concentration is determined by analysis of a sample of the blood using a blood analyser. Blood analysers are commonly present in clinical environments in order to analyse blood samples from patients. Therefore, it is highly likely that the user will have convenient access to such an analyser. By taking a sample of the blood at the same time as measuring the second value of the characteristic, while the sensor 4 is exposed to the blood, the second concentration can be determined from the sample and used to calibrate the sensor 4 with the first value.

In an embodiment, step S16 is performed in vivo. For example, in the embodiments of the component shown in FIGS. 2 and 3, the component is at least partially inserted into the body of a patient, and the luminescent compound 9 is exposed to bodily fluids. The luminescent compound 9 may be exposed to blood, as already mentioned above, or may also be exposed to other fluids such as interstitial fluid, urine, etc.

In an embodiment, step S16 is performed while the luminescent compound 9 is exposed to a pre-prepared fluid containing the analyte at the known second concentration. Using a pre-prepared fluid has the advantage that the fluid is prepared to have a known concentration of the analyte, and so no separate determination of the concentration of the analyte is needed. In an embodiment, step S12 comprises assembling the sensor 4 into a flow line for biological fluids in a medical device, wherein the pre-prepared fluid is a priming fluid for use in setup of the medical device. This is a particularly convenient situation for use of a pre-prepared fluid, because setup of some medical devices (for example dialysis systems) requires a priming fluid to be passed through the flow line in the setup of the medical device. Using this to provide the known second concentration means that no additional steps are needed in the setup of the sensor 4 to measure the second value.

In step S18, the method comprises determining parameters representing the dependence of the characteristic of the luminescence on concentration of the analyte using the first value and the second value. The parameters may be parameters of a mathematical model describing the dependence of the characteristic of the luminescence on the concentration of the analyte. As discussed above, the interaction between the analyte and the luminescent compound affects the luminescent compound 9 and its luminescence in a variety of ways. Depending on the particular combination of analyte and luminescent compound 9, different models may be appropriate for the dependence of the characteristic on the concentration of the analyte. The output of the method is calibration data 40 comprising the determined parameters representing the dependence of the characteristic of the luminescence on concentration of the analyte.

In an embodiment, the dependence of the characteristic used in step S18 is modelled using a one to one host-guest binding model. An example of a combination of analyte and luminescent compound 9 where this model would be appropriate is the sensing of pH (or $CO_2$ concentrations) using HPTS. This type of model assumes that a single molecule of analyte binds ($H^+$) with each molecule of the luminescent compound, or in the case of carbon dioxide one molecule of carbon dioxide interacts with the HPTS ion pair. Other combinations are described in relation to the luminescent compounds disclosed above, for example the sensing of sodium with moiety (I), the sensing of potassium with moiety (II), and the sensing of calcium with moiety (III).

Eq. 1 is an example of a one-to-one host-guest binding model, where the dependence of the characteristic C on the concentration of the analyte [X] is modelled using the following equation:

$$C = \frac{C_0 + [X]KC_\infty}{1 + [X]K} \qquad \text{Equation 1}$$

wherein $C_0$ is a value of the characteristic of the luminescence of the luminescent compound when the concentration of the analyte is zero, $C_\infty$ is a value of the characteristic of the luminescence of the luminescent compound when the concentration of the analyte is infinite, and K is a strength of association between the luminescent compound 9 and the analyte. Where this particular model is used, step S18 comprises determining $C_0$ and $C_\infty$.

Figure 8:
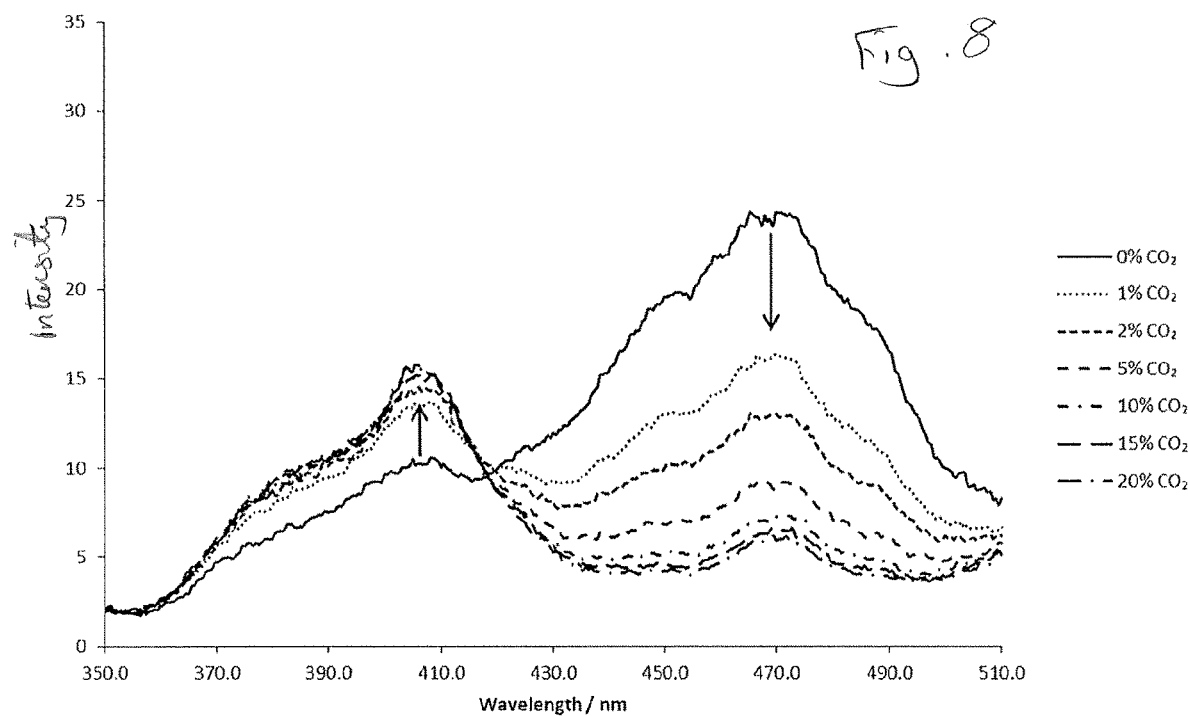
FIG. 8 is a graph illustrating the effect of a change in analyte concentration on measurements of a characteristic of the luminescence of a luminescent compound.
Figure 9:
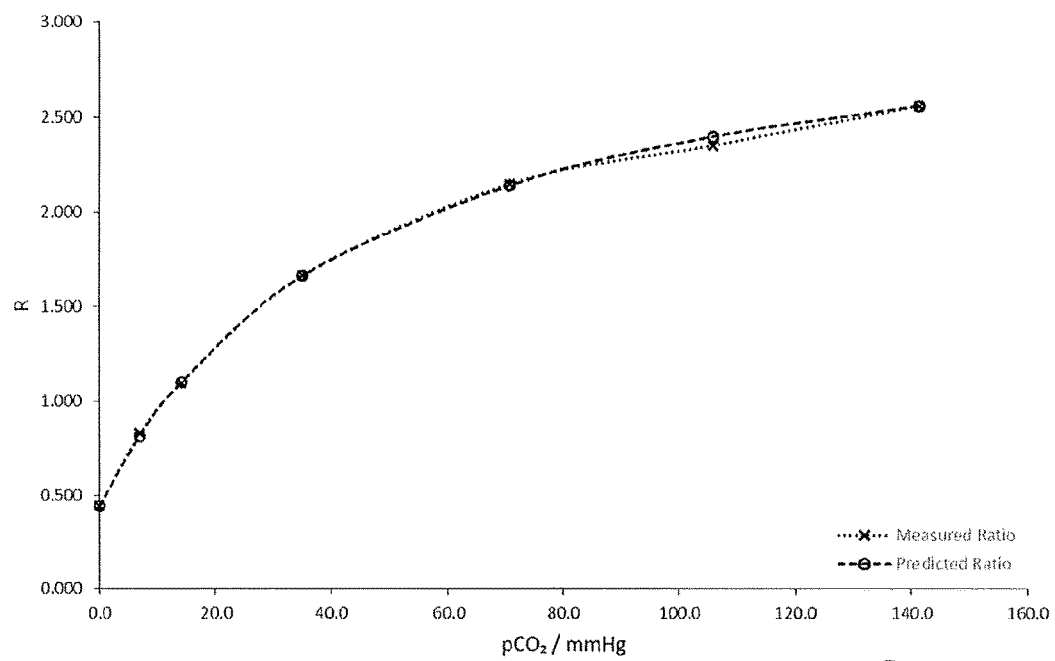
FIG. 9 is a graph of a fit of measured values of the characteristic of the luminescence to a model of the dependence of the characteristic on the concentration of the analyte.

FIG. 9 shows a comparison of the predicted value of the characteristic of the luminescence based on Eq. 1, compared to the measured value of the characteristic. In the case of FIG. 9, the characteristic is the ratio of intensity at two different wavelengths, the luminescent compound is HPTS, having an emission spectrum as shown in FIG. 8, and the analyte is carbon dioxide. The measurements of intensity are made at the wavelengths of the two peaks shown in FIG. 8 (405 nm/470 nm). FIG. 9 demonstrates that the characteristic of the luminescence fits the quadratic one-to-one host-guest binding model of Eq. 1.

Traditionally, to calibrate a sensor 4 where the model of Eq. 1 is appropriate, at least three calibration points would be needed to fit the quadratic curve and allow $C_0$, $C_\infty$, and K to be determined. However, although the characteristic of the luminescence measured by the sensor 4 will vary as the component is connected to different sensors, or if the sensor 4 is connected to different sensor apparatus, some of the parameters will remain the same. In particular, the association strength should be a constant for a particular combination of analyte and luminescent compound 9, depending on their chemical interaction. Therefore, the strength of association, given by K in Eq. 1 can be determined at the time of manufacture of the component, and it is not necessary to determine this parameter during calibration, thereby reducing the number of measurements needed to complete the calibration of the sensor 4. If the manufacturing process is generating consistently performing components, then during the calibration it should only be necessary to determine $C_0$, $C_\infty$. Therefore, in an embodiment, step S18 comprises using a predetermined value for a strength of association between the luminescent compound 9 and the analyte.

The one-to-one host-guest binding model is one where the value of the characteristic of the luminescence at zero analyte concentration, i.e. $C_0$ in Eq. 1, is a parameter of the dependence. Therefore, when the first known concentration is zero, $C_0$ can be directly determined in step S18 as the value of the characteristic measured in step S14. The value of $C_\infty$ can be determined in step S18 using $C_0$ and the value of the characteristic measured in step S16 using the following equation:

$$C_\infty = \frac{C_2(1 + [X_2]K) - C_0)}{[X_2]K} \qquad \text{Equation 2}$$

where $C_2$ is the value of the characteristic measured in step S16, when the concentration of the analyte is $[X_2]$. Where the first known concentration is not zero, the value of C may also be determined in step S18 using both values of the characteristic measured in steps S14 and S16.

For some luminescent compounds, the luminescence depends on the temperature of the luminescent compound 9. If steps S14 and S16 are performed at the same temperature as subsequent measurements of the concentration of the analyte are to be made after calibration, then there is no need to take account of temperature variation. This may be particularly true in situations where the expected variation in temperature during later operation is likely to be small, and the effect on the characteristic of the luminescence likely to be small. Therefore, in some embodiments, the luminescence depends on the temperature of the luminescent compound 9, and the parameters determined in step S18 represent the dependence of the characteristic of the luminescence on the concentration of the analyte at a predetermined temperature.

However, in other cases, the temperature variation during later operation may be expected to be substantial, or it may not be convenient to perform steps S14 and S16 at the same temperature as expected for later operation. In these cases, it may be advantageous to account for the effect of temperature on the characteristic of the luminescence of the luminescent compound 9. Therefore, in some embodiments, the luminescence depends on the temperature of the luminescent compound 9, and the parameters determined in step S18 represent the dependence of the characteristic of the luminescence on both the concentration of the analyte and the temperature of the luminescent compound 9. In this case, the calibration data 40 comprises determined parameters representing the dependence of the characteristic of the luminescence on both the concentration of the analyte and the temperature of the luminescent compound 9. Accounting for the temperature variation is likely to increase the accuracy and reliability of the reported values.

In an embodiment, the parameters determined in step S18 include a temperature parameter representing the dependence of the characteristic of the luminescence on the temperature of the luminescent compound 9. Where the model of the dependence of the characteristic of the luminescence is given by Eq. 1, the parameters determined in step S18 include a temperature parameter α representing the dependence of the characteristic of the luminescence on the temperature of the luminescent compound 9, and $C_0$ and $C_\infty$ are modelled using the following dependence on the temperature T:

$$C_0(T) = C_{0c}(1 + \alpha(T - T_c)) \qquad \text{Equation 3}$$

$$C_\infty(T) = C_{\infty c}(1 + \alpha(T - T_c)) \qquad \text{Equation 4}$$

wherein $C_{0c}$ is the value of $C_0$ at temperature $T_c$, and $C_{\infty c}$ is the value of $C_\infty$ at temperature $T_c$. This model is advantageous because only a single temperature parameter α is required to model the temperature dependence of the characteristic, even though two of the parameters of Eq. 1 are temperature-dependent.

To determine the values of the parameters at different temperatures, it is necessary to measure the temperature of the luminescent compound 9. In an embodiment, step S14 comprises measuring a first temperature of the luminescent compound 9 when measuring the first value, step S16 comprises measuring a second temperature of the luminescent compound 9 when measuring the second value, and step S18 uses the first temperature and the second temperature in addition to the first value and the second value. In an embodiment, $T_c$ in Eqns. 3 and 4 may be one of the first and second temperatures. Choosing $T_c$ to be the first temperature is particularly convenient, because this enables $C_{0c}$ to be measured directly as the first value. Then $C_{\infty c}$ can be determined from:

$$C_{\infty c} = \frac{C_2(1 + [X_2]K) - C_{0c}(1 + \alpha(T_2 - T_c))}{(1 + \alpha(T_2 - T_c))([X_2]K)} \qquad \text{Equation 5}$$

where $C_2 = C([X_2], T_2)$ is the value of the characteristic measured at $T_2$ in step S16, when the concentration of the analyte is $[X_2]$, and $C_{0c}$ is the value of the characteristic measured at $T_c$ in step S14, when the concentration of the analyte is zero. The component may include a temperature sensor 20 in order to measure the temperature of the luminescent compound 9, for example as shown in FIG. 2. Alternatively, the temperature may be measured by another component and reported to the analysis system 30 to be used in determining the parameters.

In an embodiment, the temperature parameter α has a predetermined value. Similarly to the strength of association, in some embodiments, the variation of the temperature parameter between components and/or between sensor systems may be small. In particular, the variation may be sufficiently small that using a standard value obtained during manufacture does not significantly affect the accuracy of the values obtained from the model. This has the advantage that it is not necessary to determine the temperature parameter in step S18, thereby reducing the complexity of the calibration, and potentially also the time needed for calibration.

In some embodiments, the variation in the temperature parameter α may be sufficiently large between components or between sensor apparatuses that it is desirable to determine the temperature parameter in step S18. Alternatively, it may be that increased accuracy is required in some situations, and the level of accuracy provided by using a predetermined temperature parameter is insufficient for the particular application. In this case, step S14 further comprises measuring a third value of the characteristic of the luminescence of the luminescent compound 9 while the luminescent compound 9 is exposed to the analyte at the first concentration at a third temperature different from the first temperature, and measuring the third temperature of the luminescent compound 9 when measuring the third value. Step S18 uses the third value and the third temperature, in addition to the first value, the second value, the first temperature and the second temperature. Measuring the third value at the first known concentration of the analyte means that the convenience for the user is maintained, because there is still no need to provide any specialised separate calibration equipment. In this embodiment, α can be calculated using the following equation:

$$\alpha = \frac{C_3 - C_{0c}}{C_{0c}(T_3 - T_c)} \quad \text{Equation 6}$$

where $C_3$ is the third value of the characteristic measured at the third temperature $T_3$ in step S14. In an embodiment, the component may comprise a heater configured to heat the luminescent compound 9. This enables the temperature of the luminescent compound to be varied in step S14, either while the component is still inside the package, or shortly after removal of the component from the package. The third temperature should be different to the first temperature, but may be the same as the second temperature. In an embodiment, the first and second temperatures are the same, and the third temperature is different from both the first and second temperatures.

The strength of association may also depend on temperature. In an embodiment where the model of the dependence of the characteristic of the luminescence is given by Eq. 1, K is modelled using the following dependence on the temperature T:

$$K(T) = K_c \exp\left(\beta\left(1 - \frac{T_c}{T}\right)\right) \quad \text{Equation 7}$$

wherein $K_c$ is the association constant at temperature $T_c$, and β is an association temperature constant. As mentioned above, in many embodiments, the strength of association is predetermined because its variation between components is small. In some embodiments, the association temperature constant is also predetermined, and does not need to be measured during calibration of the sensor 4.

A worked example of carrying out the calibration method will now be provided. The model described above and given in Eqns. 1 to 7 is used for the dependence of the characteristic of the luminescence on analyte concentration and temperature. The values of $K_c$ and β are predetermined, and so do not need to be determined during calibration of the sensor 4. The parameters to be determined are therefore $C_{0c}$, $C_{\infty c}$, and α. The component is provided in step S10, and assembled into the sensor in step S12.

In step S14, $C_{0c}$ is measured directly at the first temperature $T_1$ (e.g. at room temperature) by choosing the first concentration as zero, i.e. with [X]=0 and $T_1=T_c$ in Eq. 1 such that the first value $C_1=C(0, T_1=T_c)=C_{0c}$. $C_{0c}$ may be measured either before or shortly after removing the component from the package, depending on the design of the component and the package 31 as discussed above.

Also in step S14, a third value of the characteristic is measured at a third temperature while the luminescent compound 9 is exposed to the analyte at the first concentration of zero. Thereby in step S18, α can be determined from the third value $C_3=C(0, T_3)$ by using Eq. 6.

Following this, $C_{\infty c}$ is the only remaining parameter to determine in step S18. In step S16, the second value $C_2$ of the characteristic is measured at the second temperature $T_2$ while the luminescent compound 9 is exposed to the analyte at the second concentration $[X_2]$, such that $C_2=C([X_2], T_2)$. Thereby $C_{\infty c}$ can be determined in step S18 using Eq. 5.

In this manner, all of the parameters in the temperature-dependent case can be determined from the three values of the characteristic measured at the three temperatures. The manner in which the parameters are determined for two variations of this method are summarised in Table 1 below.

TABLE 1

| $C_{0c}$ | $C_{\infty c}$ | α | $K_c$ | β |
|---|---|---|---|---|
| Measure at first temperature (e.g. room temperature) | Calculate from 2 values of characteristic measured at different known temperatures (Eq. 7) | Use predetermined value | Use predetermined value | Use predetermined value |
| Measure at sensing temperature | Calculate from 2 values of characteristic measured at different known temperatures (Eq. 7) | Ramp temperature when measuring $C_{0c}$ to determine directly (Eq. 6) | Use predetermined value | Use predetermined value |

There are multiple ways to implement the options above. A suitable calibration method for an interstitial sensor such as that in FIG. 4 would be:

1. Measure $C_{0c}$ at room temperature and obtain a value for $C_0(T)$ at the sensing temperature (i.e. the temperature at which subsequent determination of analyte concentration is to be made) by using Eq. 3 and a predetermined value for α.
2. Apply the sensor to the patient and measure the second value of the characteristic.
3. Use a blood sample taken at the same time as application of the sensor to determine the second concentration of the analyte, and thereby determine $C_{\infty c}$ using Eq. 2 and default values for $K_c$, α, and β.

The two variations of Table 1 both implement a2-point calibration method, where 2-point means that only two different values of analyte concentration are needed. The 2-point calibration method allows the rejection of sensors that have low modulations and still serves as a performance validation for sensors such as the intravascular sensor of FIG. 3. Modulation is defined using the following equation:

$$\text{Modulation} = 100\left(\frac{C - C_0}{C}\right) \quad \text{Equation 8}$$

Figure 10:
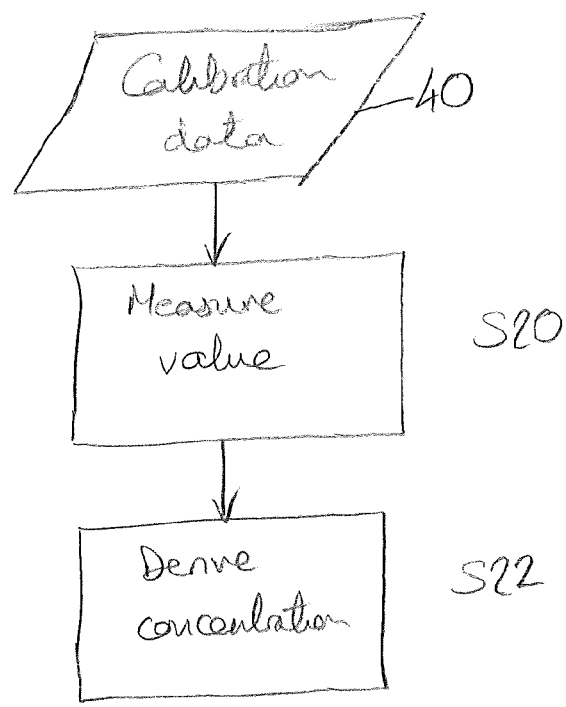
FIG. 10 is a flowchart of a method of measuring a concentration of an analyte in a sample using the sensor apparatus shown in FIG. 1.

Following calibration of the sensor using the method of calibration discussed above, the sensor can be used to measure the concentration of an analyte in a sample. An embodiment of a method of measuring the concentration of an analyte in a sample using the sensor apparatus of FIG. 1 is shown in FIG. 10. As discussed above, the sensor 4 comprises a luminescent compound 9 having a luminescence that depends on the concentration of the analyte, and a detector 14 configured to detect light emitted by the luminescent compound 9.

In step S20, the method comprises measuring a value of the characteristic of the luminescence of the luminescent compound 9 while exposed to the sample. The value of the characteristic may be measured using one of the techniques discussed above, depending on the nature of the luminescent compound and the configuration of the light source and detector. In an embodiment where the luminescence depends on the temperature of the luminescent compound 9, and the parameters represent the dependence of the characteristic of the luminescence on both the concentration of the analyte and the temperature of the luminescent compound 9, step S20 further comprises measuring a temperature of the luminescent compound 9 while exposed to the sample.

In an embodiment, the sample is a biological fluid, and the value of the characteristic of the luminescence is measured in vivo. The biological fluid may be, for example, blood or interstitial fluid. The method is particularly suited for clinical applications, and so blood is an advantageous target for determination of concentrations of analytes. The sensors shown in FIGS. 3 and 4 are suited for in vivo measurements.

In an alternative embodiment, the sample is a biological fluid, and the value of the characteristic of the luminescence is measured in vitro. Sensors such as that shown in FIG. 2 are suited for in vitro measurements, where the biological fluid is circulated outside of the patient's body. For example, in an embodiment the method of measuring the concentration may further comprise assembling the sensor 4 into a flow line for biological fluids in a medical device, wherein the sample is present in the flow line. This would be particularly advantageous in, for example, monitoring of a patient undergoing dialysis or extracorporeal membrane oxygenation of blood.

In step S22, the method comprises deriving the concentration of the analyte in the sample using the measured value and the determined parameters representing the dependence of the characteristic of the luminescence on concentration of the analyte. The calibration data 40 is an input of the method and comprises the determined parameters from calibration of the sensor 4. Using the above model, the parameters of the model are $C_{0c}$, $C_{\infty c}$, α, $K_c$, and β. Combining Eqns. 1, 3, 4, and 7 results in the following equation for the concentration:

$$C([X], T) = \frac{\left(C_{0c} + [X]K_c e^{\beta\left(1-\frac{T_c}{T}\right)}\right)(1 + \alpha(T - T_c))}{1 + [X]K_c e^{\beta\left(1-\frac{T_c}{T}\right)}} \quad \text{Equation 9}$$

which can be rearranged to:

$$[X] = \frac{C_{0c}(1 + \alpha(T - T_c)) - C}{K_c e^{\beta\left(1-\frac{T_c}{T}\right)}(C - (1 + \alpha(T - T_c)))} \quad \text{Equation 10}$$

where C is the value of the characteristic measured at temperature T in step S20. Using Eq. 9, the concentration of the analyte can be derived using the parameters determined during calibration, and the measurements made in step S20.

The invention claimed is:

1. A method of calibrating a sensor comprising a luminescent compound having a luminescence that depends on the concentration of an analyte, and a detector configured to detect light emitted by the luminescent compound, the method comprising:
   providing a component comprising the luminescent compound in a package that maintains exposure of the luminescent compound to the analyte at a known first concentration;
   assembling the component into the sensor and, during a predetermined time period following the removal of the component from the package within which the luminescent compound remains exposed to the analyte at the first concentration, measuring a first value of a characteristic of the luminescence of the luminescent compound while exposed to the analyte at the first concentration;
   measuring a second value of the characteristic of the luminescence of the luminescent compound while exposed to the analyte at a known second concentration different from the first concentration; and
   determining parameters representing the dependence of the characteristic of the luminescence on concentration of the analyte using the first value and the second value.

2. A method according to claim 1, wherein the predetermined time period is at most 5 minutes.

3. A method according to claim 1, wherein the first concentration is zero.

4. A method according to claim 1, wherein the step of measuring a second value is performed while the luminescent compound is exposed to blood containing the analyte at the second concentration.

5. A method according to claim 4, wherein the second concentration is determined by analysis of a sample of the blood using a blood analyser.

6. A method according to claim 4, wherein the step of measuring a second value is performed in vivo.

7. A method according to claim 1, wherein the step of measuring a second value is performed while the luminescent compound is exposed to a pre-prepared fluid containing the analyte at the known second concentration.

8. A method according to claim 7, further comprising assembling the sensor into a flow line for biological fluids in a medical device, wherein the pre-prepared fluid is a priming fluid for use in setup of the medical device.

9. A method according to claim 1, wherein the luminescence depends on the temperature of the luminescent compound, and the parameters represent the dependence of the characteristic of the luminescence on both the concentration of the analyte and the temperature of the luminescent compound.

10. A method according to claim 9, wherein the method further comprises: measuring a first temperature of the luminescent compound when the step of measuring the first value is performed; and measuring a second temperature of the luminescent compound when the step of measuring the second value is performed, and wherein the step of determining parameters representing the dependence of the characteristic of the luminescence on concentration of the analyte uses the first temperature and the second temperature in addition to the first value and the second value.

11. A method according to claim 10, wherein the parameters include a temperature parameter representing the dependence of the characteristic of the luminescence on the temperature of the luminescent compound.

12. A method according to claim 11, wherein the temperature parameter has a predetermined value.

13. A method according to claim 11, wherein the method further comprises measuring a third value of the characteristic of the luminescence of the luminescent compound while the luminescent compound is exposed to the analyte at the first concentration at a third temperature different from the first temperature; and measuring the third temperature of the luminescent compound when the step of measuring the third value is performed, and wherein the step of determining parameters representing the dependence of the characteristic of the luminescence on concentration of the analyte uses the third value and the third temperature, in addition to the first value, the second value, the first temperature and the second temperature.

14. A method according to claim 1, wherein the luminescence depends on the temperature of the luminescent compound, and the parameters represent the dependence of the characteristic of the luminescence on the concentration of the analyte at a predetermined temperature.

15. A method according to claim 1, wherein the characteristic of the luminescence of the luminescent compound is the intensity of the luminescence.

16. A method according to claim 1, wherein the characteristic of the luminescence of the luminescent compound is a ratio of the intensity of the luminescence at two different wavelengths.

17. A method according to claim 1, wherein the dependence of the characteristic is modelled using a one to one host-guest binding model.

18. A method according to claim 17, wherein determining parameters representing the dependence comprises using a predetermined value for a strength of association between the luminescent compound and the analyte.

19. A method according to claim 17, wherein the dependence of the characteristic C on the concentration [X] of the analyte is modelled using the following equation:

$$C = \frac{C_0 + [X]KC_\infty}{1 + [X]K}$$

wherein:
$C_0$ is a value of the characteristic of the luminescence of the luminescent compound when the concentration of the analyte is zero;
$C_\infty$ is a value of the characteristic of the luminescence of the luminescent compound when the concentration of the analyte is infinite;
K is a strength of association between the luminescent compound and the analyte, and
determining parameters representing the dependence comprises determining $C_0$ and $C_\infty$.

20. A method according to claim 19, wherein:
the parameters include a temperature parameter a representing the dependence of the characteristic of the luminescence on the temperature of the luminescent compound;

and
$C_0$ and $C_\infty$ are modelled using the following dependence on the temperature T:

$$C_0(T) = C_{0c}(1 + \alpha(T - T_c))$$

$$C_\infty(T) = C_{\infty c}(1 + \alpha(T - T_c))$$

wherein:
$C_{0c}$ is the value of $C_0$ at temperature $T_c$;
$C_{\infty c}$ is the value of $C_\infty$ at temperature $T_c$.

21. A method according to claim 19, wherein K is modelled using the following dependence on the temperature T:

$$K(T) = K_c \exp\left(\beta\left(1 - \frac{T_c}{T}\right)\right)$$

wherein:
$K_c$ is the association constant at temperature Tc; and
β is an association temperature constant.

22. A method according to claim 1, wherein the component is a replaceable component of the sensor.

23. A method of measuring a concentration of an analyte in a sample using a sensor comprising a luminescent compound having a luminescence that depends on the concentration of the analyte, and a detector configured to detect light emitted by the luminescent compound, the method comprising:
calibrating the sensor using the method of claim 1;
measuring a value of the characteristic of the luminescence of the luminescent compound while exposed to the sample; and
deriving the concentration of the analyte in the sample using the measured value and the determined parameters representing the dependence of the characteristic of the luminescence on concentration of the analyte.

24. A method according to claim 23, wherein the sample is a biological fluid, and the value of the characteristic of the luminescence is measured in vivo.

25. A method according to claim 23, wherein the sample is a biological fluid, and the value of the characteristic of the luminescence is measured in vitro.

26. A method according to claim 25, further comprising assembling the sensor into a flow line for biological fluids in a medical device, wherein the sample is present in the flow line.

27. A method according to claim 24, wherein the biological fluid is blood or interstitial fluid.

28. A method according to claim 1, wherein the sensor further comprises a light source configured to excite the luminescent compound, and measuring a value of the characteristic of the luminescence of the luminescent compound comprises exciting the luminescent compound using the light source, and detecting light emitted by the luminescent compound using the detector.

29. A method according to claim 1, wherein the analyte is one of carbon dioxide, hydrogen ions, sodium, potassium, magnesium, and calcium.

30. A method according to claim 1, wherein the luminescent compound comprises a fluorescent compound.

31. A method according to claim 30, wherein the fluorescent compound comprises 8-hydroxypyrene-1,3,6-trisulfonic acid.

* * * * *